(12) United States Patent
Barras et al.

(10) Patent No.: US 11,912,976 B2
(45) Date of Patent: Feb. 27, 2024

(54) CELL CULTURE MONITORING SYSTEM

(71) Applicant: CEIDOS SA, Sion (CH)

(72) Inventors: Léonard Barras, Sion (CH); Sébastien Walpen, Sion (CH)

(73) Assignee: CEIDOS SA, Sion (CH)

( * ) Notice: Subject to any disclaimer, the term of this patent is extended or adjusted under 35 U.S.C. 154(b) by 0 days.

(21) Appl. No.: 17/774,348

(22) PCT Filed: Nov. 3, 2020

(86) PCT No.: PCT/EP2020/080836
§ 371 (c)(1),
(2) Date: May 4, 2022

(87) PCT Pub. No.: WO2021/089558
PCT Pub. Date: May 14, 2021

(65) Prior Publication Data
US 2022/0389366 A1    Dec. 8, 2022

(30) Foreign Application Priority Data
Nov. 8, 2019    (EP) ..................................... 19208209

(51) Int. Cl.
*C12M 1/36* (2006.01)
*C12M 1/00* (2006.01)
*C12M 1/34* (2006.01)

(52) U.S. Cl.
CPC ............ *C12M 41/36* (2013.01); *C12M 23/22* (2013.01)

(58) Field of Classification Search
CPC ............................. C12M 23/22; C12M 41/36
See application file for complete search history.

(56) References Cited

FOREIGN PATENT DOCUMENTS

| EP | 3196631 | 7/2017 |
| FR | 3025802 | 3/2016 |

(Continued)

OTHER PUBLICATIONS

International Search Report and Written Opinion as issued by the International Searching Authority, dated Feb. 4, 2021, for International Patent Application No. PCT/EP2020/080836; 14 pages.

(Continued)

*Primary Examiner* — Lydia Edwards
(74) *Attorney, Agent, or Firm* — Faegre Drinker Biddle & Reath LLP

(57) ABSTRACT

A cell culture monitoring system comprising a monitoring apparatus for coupling to a culture tank containing a cell culture medium therein, and a fluid circulation system for fluidic coupling to the cell culture tank the fluid circulation system comprising a dielectrophoresis cartridge for connection to the cell culture tank via supply and return conduits, the dielectrophoresis cartridge comprising a base and an electrode support having electrodes in or on the electrode support, the electrodes configured for traveling wave dielectrophoresis and comprising a measurement zone arranged above a measuring chamber formed between the electrode support and a floor of the base forming a measuring chamber therebetween, whereby cells in a liquid medium flowing through the measuring chamber are subject to a traveling wave dielectrophoresis force orthogonal to a direction of flow of said liquid through said measuring chamber.

15 Claims, 8 Drawing Sheets

(56) References Cited

FOREIGN PATENT DOCUMENTS

| JP | 2016133314 | 7/2016 | |
|----|------------|--------|---|
| WO | 2010/041231 | 4/2010 | |
| WO | 2010/113994 | 10/2010 | |
| WO | WO-2018183126 A1 * | 10/2018 | .......... B01F 13/0091 |

OTHER PUBLICATIONS

"Continuous separation of viable cells by travelling wave dielectrophoresis", Van Den Driesche S., et al., ScienceDirect, Procedia Engineering, vol. 5, Jan. 1, 2010; 4 pages.

* cited by examiner

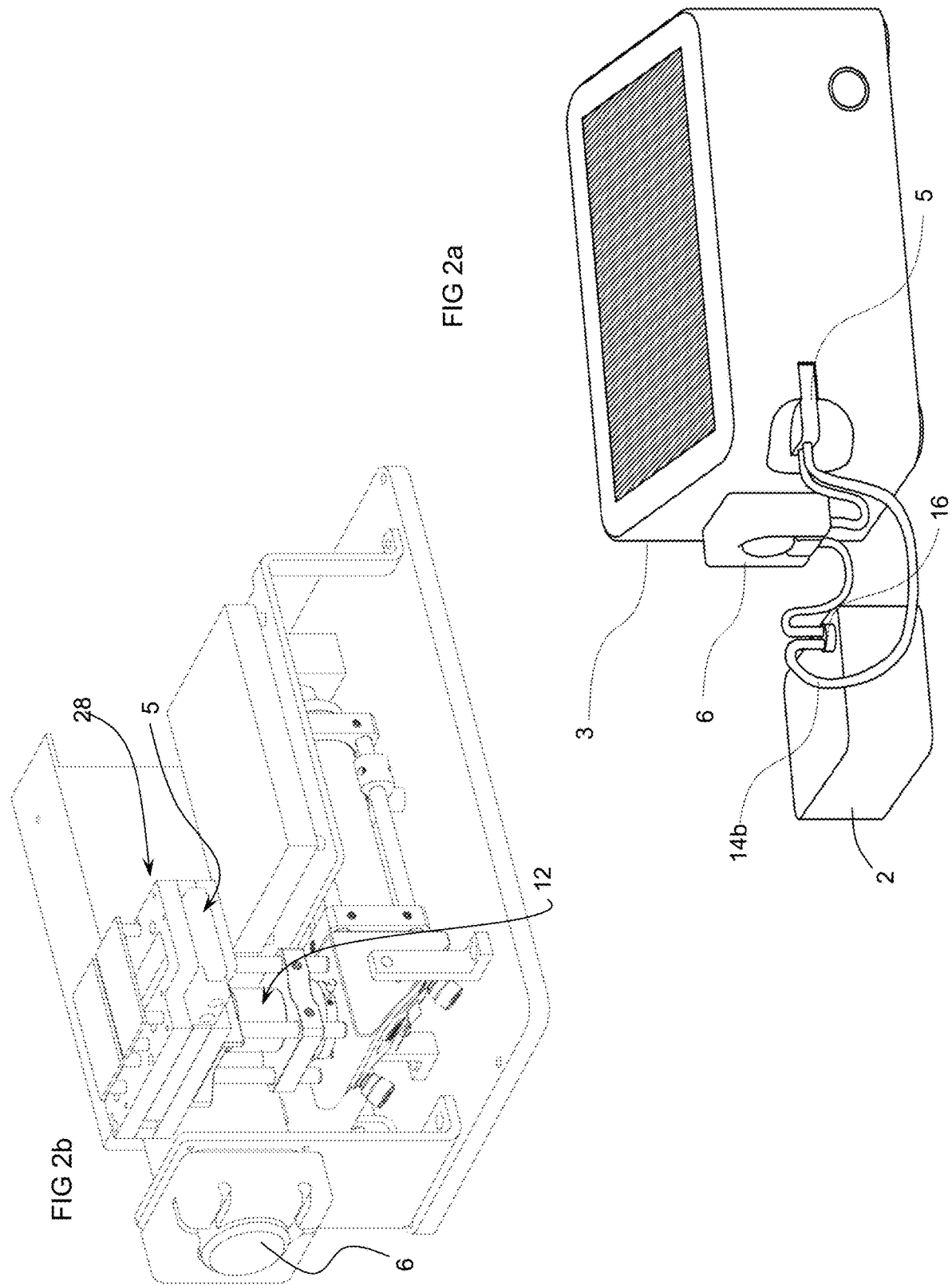

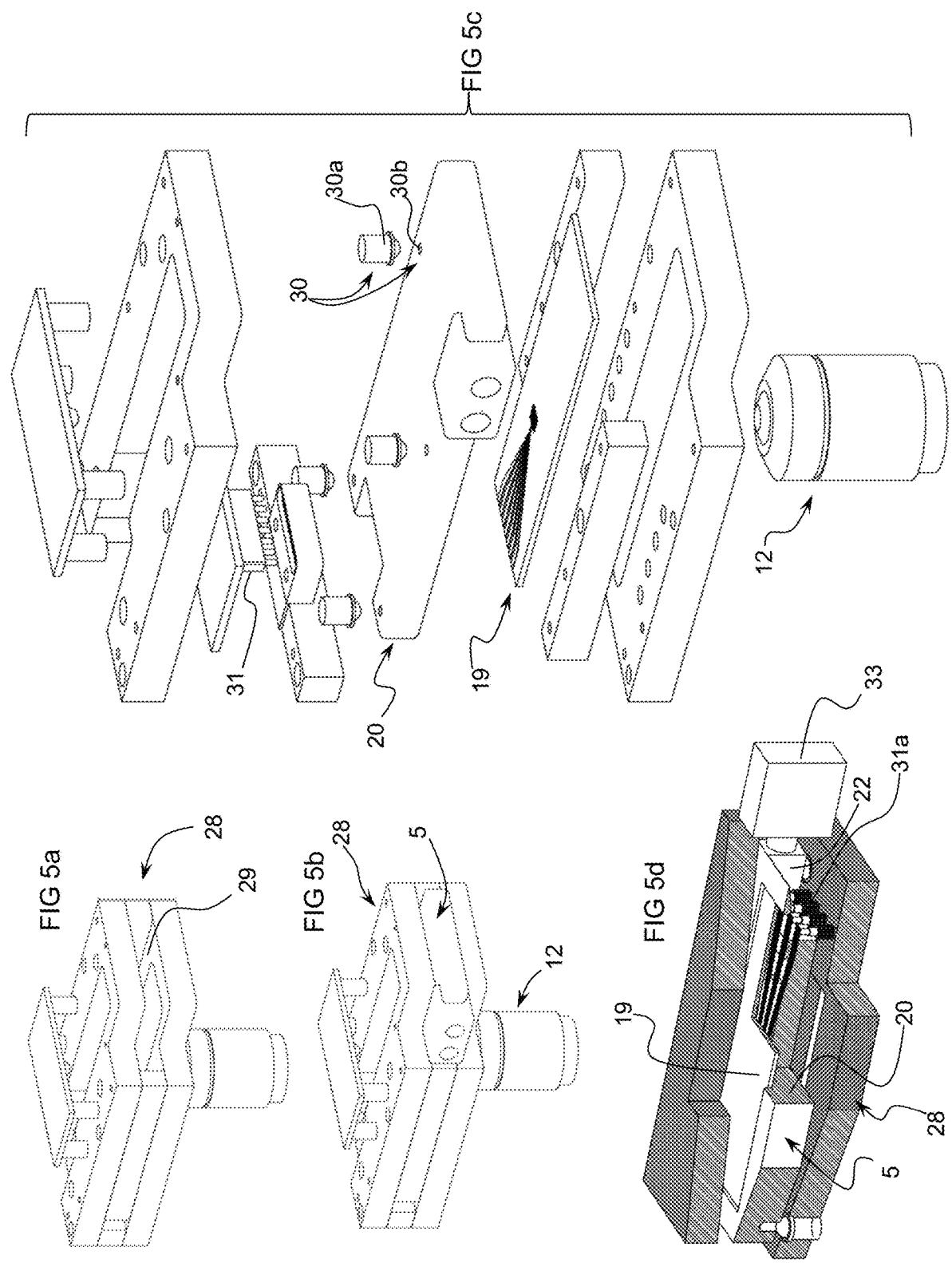

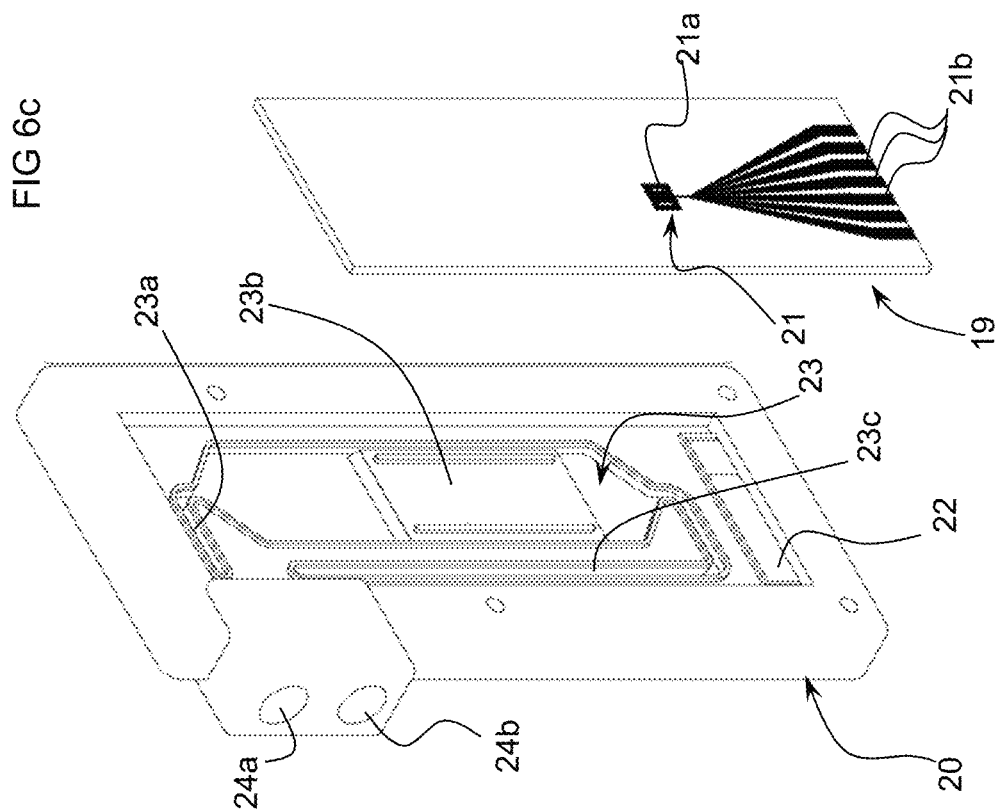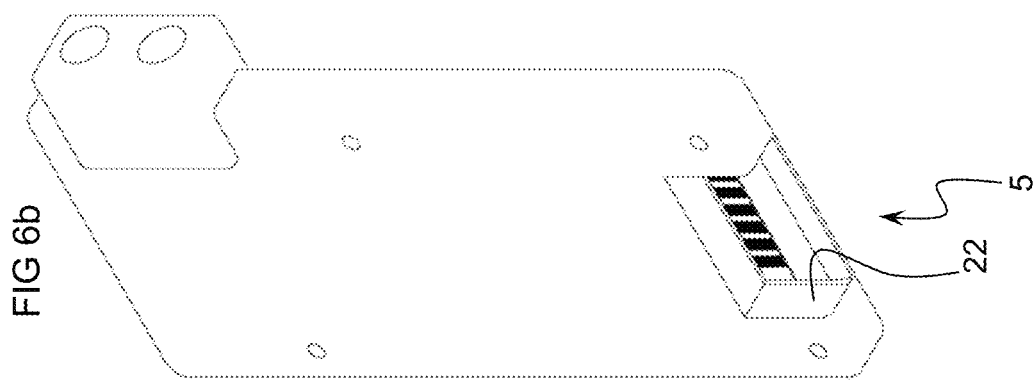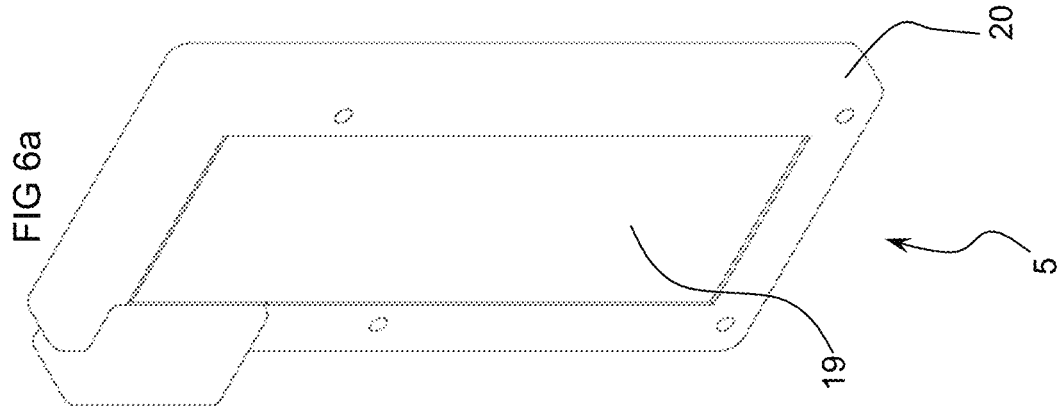

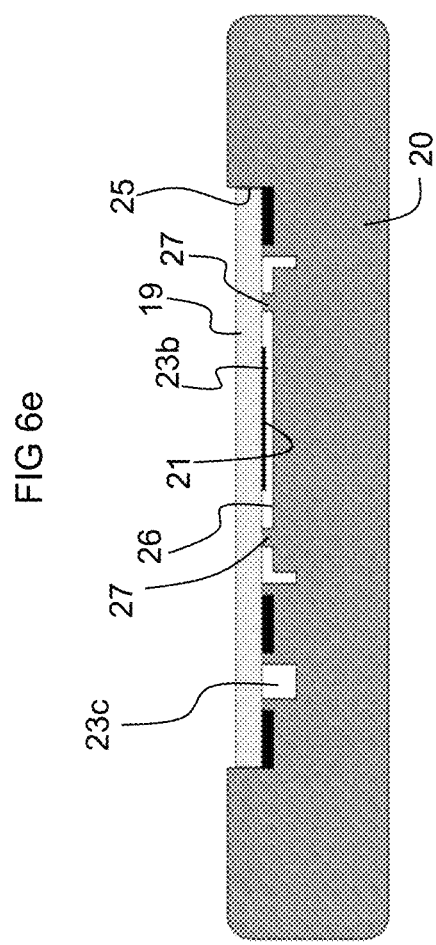
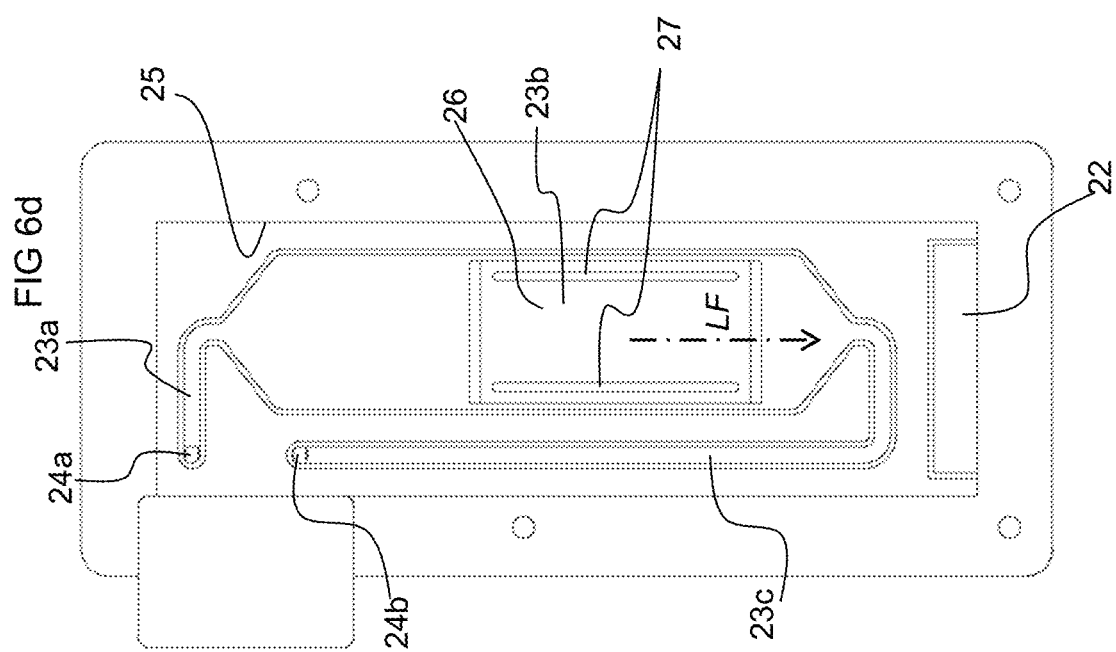

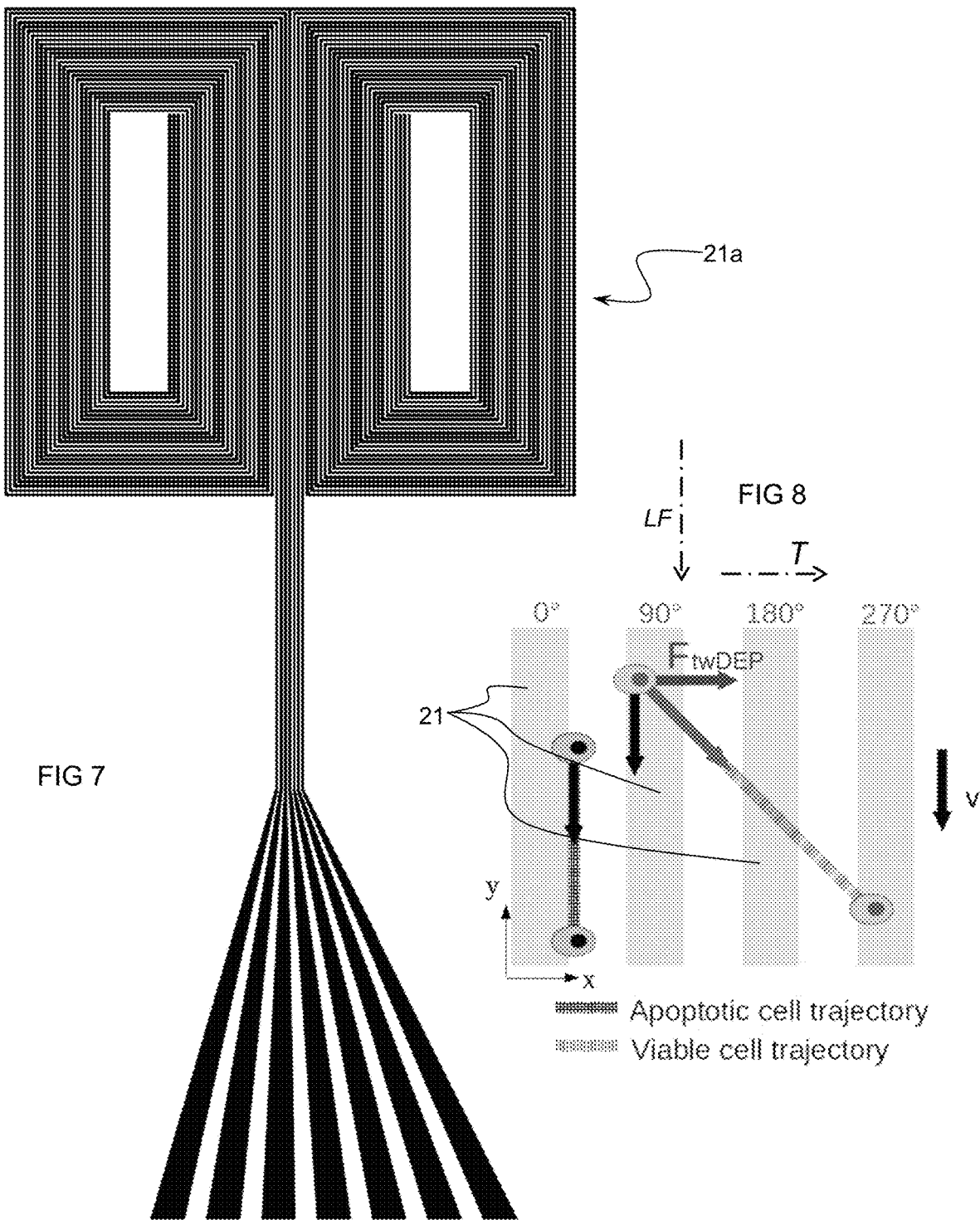

CELL CULTURE MONITORING SYSTEM

CROSS-REFERENCE TO RELATED APPLICATIONS

The present application is a national stage entry of International (PCT) Patent Application Number PCT/EP2020/080836, filed Nov. 3, 2020, which claims priority to European Patent Application Number 19208209.7, filed Nov. 8, 2019, the complete disclosures of which are expressly incorporated herein by reference.

The present invention relates to a system for monitoring the culture of cells in a liquid medium.

The emergence of cell therapies and cell based product is leading to an increased need for accurate and timely control of cell cultures. Cell cultures may also be used for bioproduction for instance of antibodies and vaccines. Many steps of conventional culture processes need human intervention, in particular for cell counting and cell viability measurement. Each intervention increases the risk of contamination and the final cost of the therapy. The loss of a therapy batch due to error or contamination has dramatic consequences for the patient.

In view of the foregoing, an object of the invention is to provide a cell culture monitoring system that allows for accurate control of cell growth and reduces the risk of contamination in an economical manner.

It is advantageous to provide a cell culture monitoring system that is reliable.

It is advantageous to provide a cell culture monitoring system that allows continuous or frequent analyses of the state of cells during culture in an economical and sterile manner.

Continuous measurements of viability would allow to detect cell culture disease at an early stage.

Objects of the invention have been achieved by providing a cell culture monitoring system according to claim 1.

Disclosed herein is a cell culture monitoring system comprising a monitoring apparatus for coupling to a culture tank containing a cell culture medium therein, and a fluid circulation system for fluidic coupling to the cell culture tank, the fluid circulation system comprising a dielectrophoresis cartridge for connection to the cell culture tank via supply and return conduits. The dielectrophoresis cartridge comprises a base and an electrode support having electrodes in or on the electrode support, the electrodes configured for traveling wave dielectrophoresis and comprising a measurement zone arranged above a measuring chamber formed between the electrode support and a floor of the base forming a measuring chamber therebetween, whereby cells in a liquid medium flowing through the measuring chamber are subject to a traveling wave dielectrophoresis force orthogonal to a direction of flow of said liquid through said measuring chamber. The monitoring apparatus comprises a computing unit, an image capture system connected to the computing unit, and a cartridge holder portion for receiving said dielectrophoresis cartridge such that the image capture system may detect cells flowing through said measuring chamber.

In an advantageous embodiment, at least the base of the dielectrophoresis cartridge is made of a polymer, preferably a transparent polymer.

In an advantageous embodiment, the electrode support is made of a transparent polymer or glass.

In an advantageous embodiment, the dielectrophoresis cartridge comprises an outlet and an inlet configured for coupling to tubes of a supple polymer forming said supply and return conduits.

In an advantageous embodiment, the electrodes are formed on an inner surface of the electrode support bounding the measuring chamber and having contact portions extending to an electrode connection window formed in the base for plugging contact to complementary spring contacts of the monitoring apparatus, the electrode connection window being sealingly separated from the measuring chamber.

In an advantageous embodiment, the measuring chamber comprises a raised floor and lateral guides defining a gap between the floor and electrode support.

In an advantageous embodiment, said electrodes comprise a measurement zone formed by one or more spiraling conductive tracks.

In an advantageous embodiment, said electrodes consist of four to ten electrodes, preferably four to eight electrodes.

In an advantageous embodiment, the electrodes are arranged in the measurement zone in two sets in mirror image symmetry.

In an advantageous embodiment, the cartridge holder portion of the monitoring apparatus comprises a cartridge holder slot configured for slidable insertion of the dielectrophoresis cartridge therein.

In an advantageous embodiment, the cartridge holder portion comprises locating elements engaging in complementary locating elements in the dielectrophoresis cartridge for positioning and securing the dielectrophoresis cartridge in a measurement position.

In an advantageous embodiment, the locating elements comprise spring protuberances or spring resist portions on either the cartridge holder portion or the dielectrophoresis cartridge.

In an advantageous embodiment, the image capture system comprises a microscope connected to an image processing circuit of the computing unit configured for digital analysis of the trajectory of the cells captured by the image capture system.

In an advantageous embodiment, the computing unit comprises a signal generator connected via the connector to the electrodes of the dielectrophoresis cartridge configured to generate a traveling wave dielectrophoresis signal in the measurement zone of the electrodes.

In an advantageous embodiment, the measuring chamber between electrode and floor is in the range of 10 to 200 µm.

In an advantageous embodiment, the cell culture tank is separate from the monitoring apparatus and comprises a fluidic connector for connection to supply and return conduits connected to the dielectrophoresis cartridge.

Further objects and advantageous features of the invention will be apparent from the claims, from the detailed description, and annexed drawings, in which:

FIG. 2a is a perspective view of a cell culture monitoring system according to an embodiment of the invention;

FIG. 2b is a perspective view of a portion of the cell culture monitoring system of FIG. 2a with a cover removed and certain internal components removed;

FIG. 5a is a perspective view of a cartridge holder portion of a monitoring apparatus of a cell culture system according to an embodiment of the invention;

FIG. 5b is a view similar to FIG. 5a with a cartridge of the cell culture monitoring system according to an embodiment of the invention, inserted in the holder;

FIG. 5d is a perspective partial cross-sectional simplified view of the cartridge and holder of FIG. 5b;

FIG. 5c is an exploded view of the elements of FIG. 5b;

FIGS. 6a and 6b are perspective views of the cartridge according to an embodiment of the invention;

FIG. 6c is an exploded perspective view of the cartridge according to an embodiment of the invention;

FIG. 6d is a plan view of a base of the cartridge according to an embodiment of the invention;

FIG. 6e is a cross-sectional view through the cartridge according to an embodiment of the invention;

FIG. 7 is a view of electrodes of a dielectrophoresis cartridge according to an embodiment of the invention;

FIG. 8 is a schematic simplified representation of the trajectory of cells relative to the electrodes when subject to dielectrophoresis;

Figure 1:
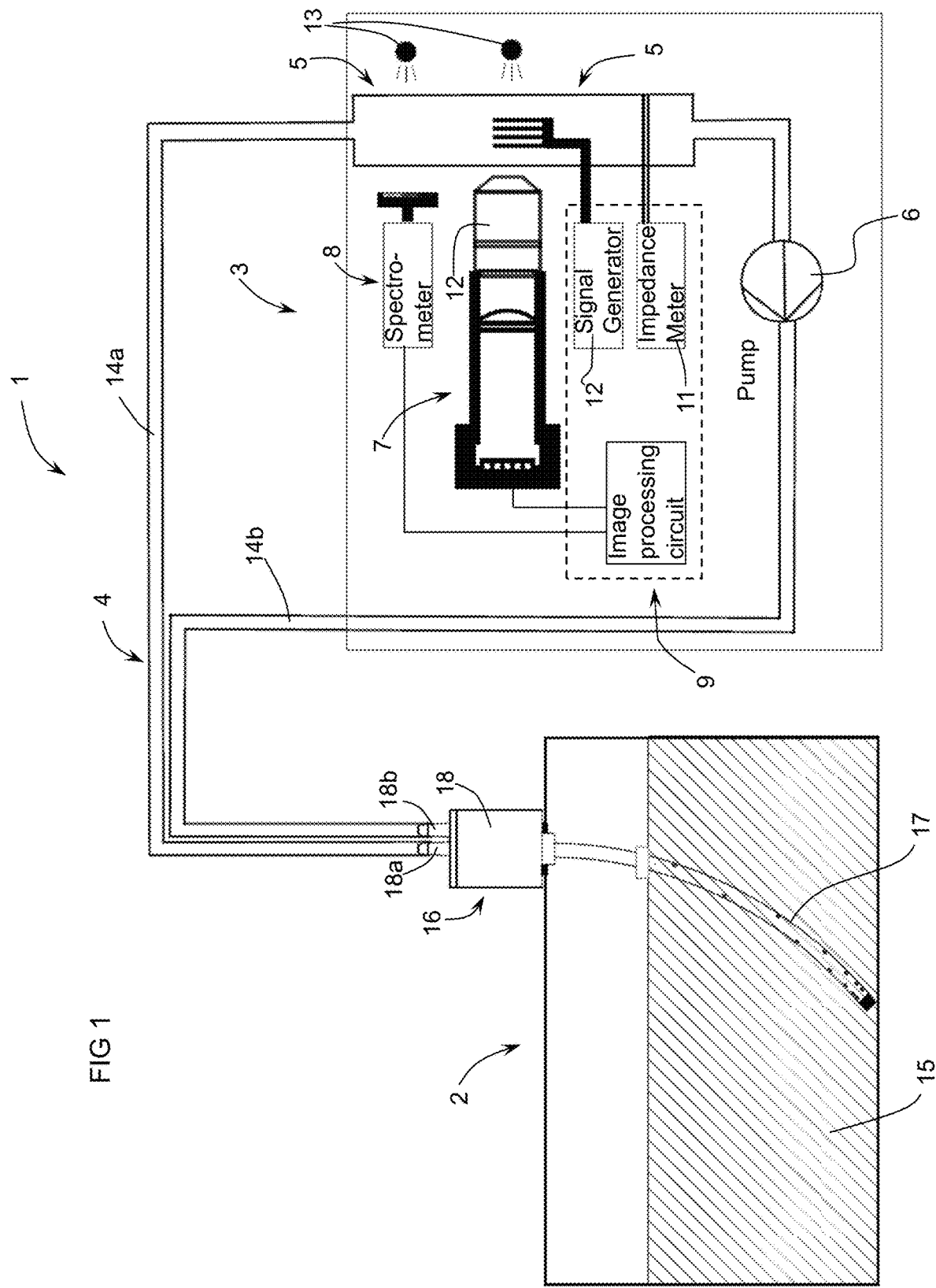
FIG. 1 is a schematic representation of a cell culture monitoring system according to an embodiment of the invention.
Figure 4:
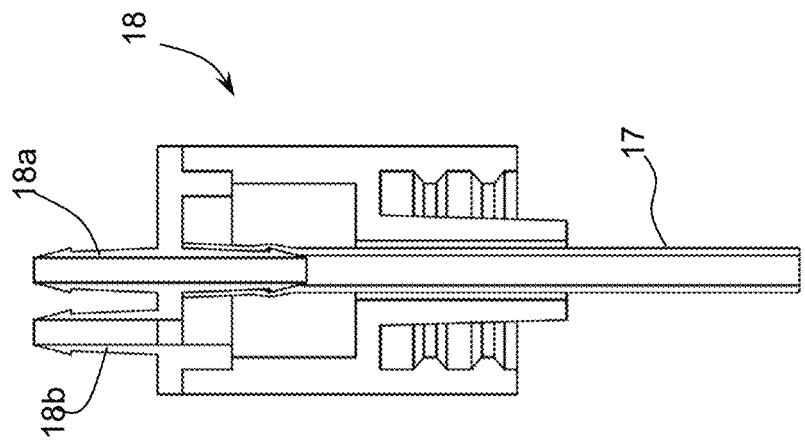
FIG. 4 is a cross-sectional view of a fluidic connector of the cell culture tank.
Figure 3B:
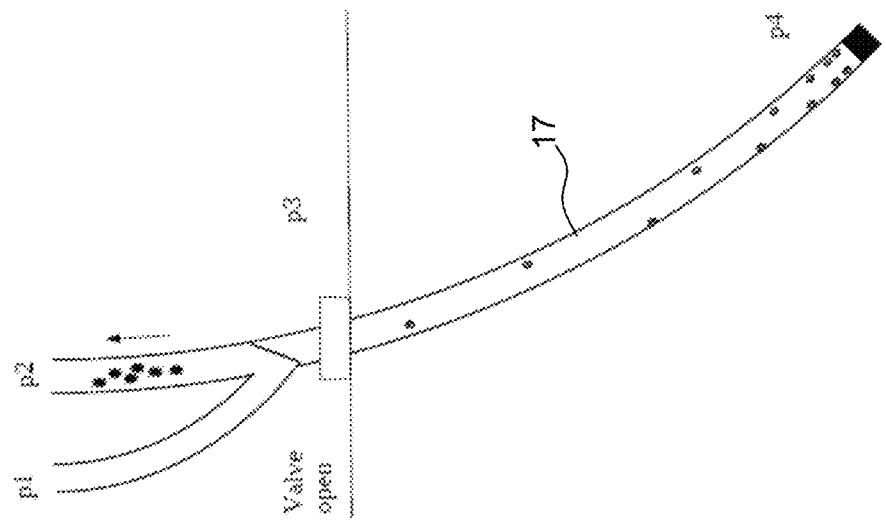
FIGS. 3a and 3b are schematic views of a tube inserted in a cell culture tank 2 of a cell culture monitoring system according to an embodiment of the invention.
Figure 3A:
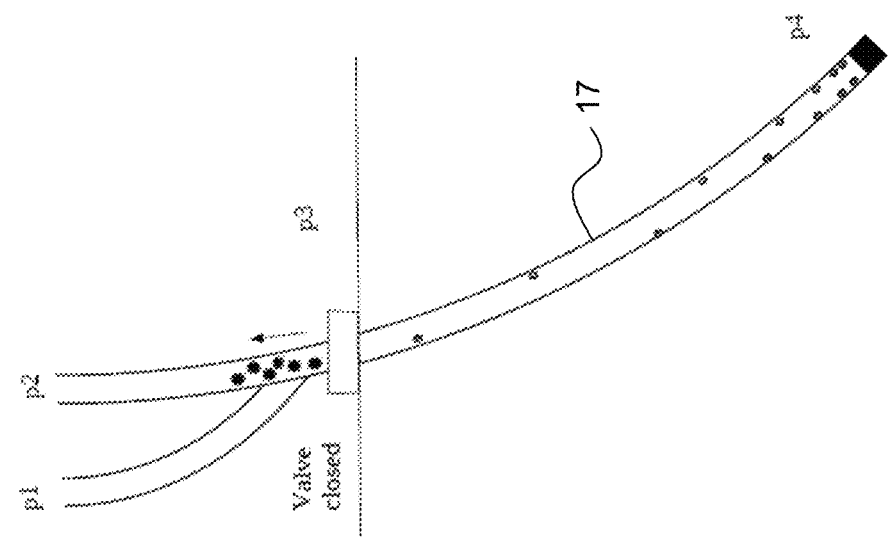

Referring to the figures, a cell culture monitoring system 1 according to embodiments of the invention comprises a monitoring apparatus 3, a cell culture tank 2, and a fluid circulation system 4 for transporting a cell culture medium containing cells to be observed between the cell culture tank and the monitoring apparatus.

The monitoring apparatus 3 comprises an image capture system 7, a spectrometer 8, a computing unit 9, and a cartridge holder portion 28 for receiving a dielectrophoresis cartridge 5 of the fluid circulation system 4.

The fluid circulation system 4 comprises the dielectrophoresis cartridge 5 and conduits 14a, 14b interconnecting the dielectrophoresis cartridge 5 to the cell cartridge tank 2. The fluid circulation system 4 further comprises a pump 6 that may be mounted or formed part of the monitoring apparatus 3 (as illustrated) or that may in other variants be mounted on the cell cartridge tank and electrically connected to the monitoring apparatus for control of the pump. In a preferred embodiment, the pump is mounted on the monitoring apparatus and may advantageously be in a form of a peristaltic pump. At least a portion of the supply conduit 14a comprises a flexible section of tube mounted in the peristaltic pump for pumping of the cell culture medium in a sterile manner.

The supply conduit 14a and return conduit 14b connected to the dielectrophoresis cartridge 5 and cell culture tank 2 of the fluid circulation system advantageously forms a closed circuit enabling fluid of a cell culture medium 15 contained in the cell culture tank 2 to be circulated to the dielectrophoresis cartridge 5 and back to the cell culture tank in a closed circuit. In a variant, the fluid circulation system may further comprise an exit conduit coupled to a waste channel 23 for the removal of dead (i.e. apoptotic) cells separated from live cells, or for separating different cell pheonotypes, due to their different trajectories in the dielectrophoresis cartridge. The fluidic connector 18 may be connected to the cell culture tank via a luer lock type of connection as per se well known in the art of fluidic connections, or may be interconnected by other means. The fluidic connector 18 allows flexible tubes, in particular the tank supply and return tubes, to be coupled to the connector.

The supply conduit 14a may further comprise a perforated tube 17 immersed in the cell culture medium 15, and preferably that extends to the bottom of the cell culture tank. The perforations in the tube 17 may be arranged such that there are a larger number of perforations towards the bottom of the tank and a progressively decreasing number of perforations towards the top of the tank, such that the inlet resistance decreases towards the bottom of the tank. This ensures that the sucking pressure is substantially evenly distributed in order to ensure that cell culture medium throughout the height of the cell culture tank is drawn into the supply tube for a uniform sampling over the height. A weight at the bottom of the perforated tube and a float at the top of the tube may be provided to ensure all the holes are under liquid. Other tube holding and positioning means may however be provided. Moreover, the perforated tube may comprise various shapes, for instance a "corkscrew" shape to increase uniformity of horizontal sampling. The cell culture container may further comprise mixing system, for instance rotating blades or a magnetic bar stirrer (not shown) to homogenize the cell distribution in the culture medium.

A valve may be provided in the fluidic connector 18 allowing re-circulation of cell culture medium within the supply return conduits to circulate in a closed circuit without passing through the culture tank, or to change the valve setting such that new cell culture medium drawn from the cell culture tank is pumped into the supply conduit. The functioning of the valve may depend on the analysis to be performed, for instance if the supply and return conduits are connected together, multiple recirculation of the sample medium may be passed through the dielectrophoresis cartridge for measurement, for instance for increasing the sensitivity of measurement, or new cell culture medium may be pumped into the supply conduit and return to the cell culture tank for a single pass through the dielectrophoresis cartridge.

A valve may also be provided to switch the return conduit to a waste container (not shown) in certain instances where the sample being measured is discarded and is not returned to the cell culture medium.

The dielectrophoresis cartridge 5 according to an advantageous embodiment of the invention comprises a base 20 and an electrode support 19. The base 20 may advantageously be made of a polymer material which in certain embodiments may advantageously be a transparent polymer material such as ABS (Acrylnitril-Butadien-Styrol-Copolymer). The base may advantageously be molded, for instance injection molded, or made by additive manufacturing techniques (such as 3D printing).

The electrode support 19 may be made of a polymer material, but is preferably made of glass, and comprises conductive electrodes on the glass that may be made by various per se known deposition and patterning techniques, such as chemical vapor deposition, lithography, printing, and other known metallic layer deposition techniques. In advantageous embodiments, the electrode support 19 is a part separately formed from the base and assembled to the base, for instance by adhesive bonding, ultrasound bonding, or welding. However it is also possible by way of additive manufacturing techniques to form the base, support and electrodes as a single part.

The base 20 comprises a fluidic connector portion 24 comprising an inlet 24a and an outlet 24b, and a microfluidic circuit formed within the base having channels interconnecting the inlet 24a to the outlet 24b. The base further comprises an electrode connection window 22 that allows access to contact portions 21b of the electrodes 21.

The microfluidic circuit 23 comprises an inlet channel 23a connected to the inlet 24a, flowing into a measuring chamber 23b, a return channel 23c flowing out from the measuring chamber 23b to the outlet 24b. The measurement chamber 23b may advantageously comprise a raised floor 26 that defines a channel height between the base 20 and the electrode support 19. This ensures that a very well defined gap for the fluid flowing through the measuring chamber is provided under a measuring zone 21a of the electrodes 21 positioned over the measuring chamber. The height in the measuring chamber 23 between electrode and floor 26 is preferably in the range of 10 to 200 µm.

Cells in the liquid flowing through the measuring chamber 23b are subject to a traveling wave dielectrophoresis force depending on the state of the cells. Use of dielectrophoresis electrodes to determine the state of a cell is per se a well-known concept. In conventional systems, typically cells within a liquid medium are displaced by dielectrophoresis, such displacement being indicative of the state of the cells. Dead cells are displaced less or are not subject to a traveling wave dielectrophoresis force whereby living cells are subject to the dielectrophoresis force and translate across the electrodes. In the present invention, the cells in the measuring chamber 23b are subject to a fluid flow such that they exhibit a component in the liquid flow direction LF through the measuring chamber, from the inlet towards the outlet as well as a translational movement T laterally due to the traveling wave dielectrophoresis force $F_{twDEP}$. The direction of movement of the cells is captured by the image capture system 7 and analysed by the computing unit 9.

An important advantage of the simultaneous fluid flow and translational movement by dielectrophoresis is that the vectorial component allows for very accurate and easy measurement of the state of the cells, to discriminate between healthy and dead cells as well as the state of the cells affecting the dielectrophoresis force.

Electroporation is a technique used to improve cell transfer. According to another aspect of the invention the dielectrophoresis zone in the measuring chamber may be used for this purpose. The generated electric field (amplitude dependent) increases the permeability of cell membranes and promotes the integration of vectors (e.g. viruses) into cells. Being able to move microorganisms of different sizes (e.g. viruses and cells) at different speeds through dielectrophoresis would amplify the integrations of viruses since collisions would occur. The traveling wave dielectrophoresis forces generated in the measurement chamber can therefore be used to move the microorganisms laterally in both directions and create multiple collisions.

Figure 9:
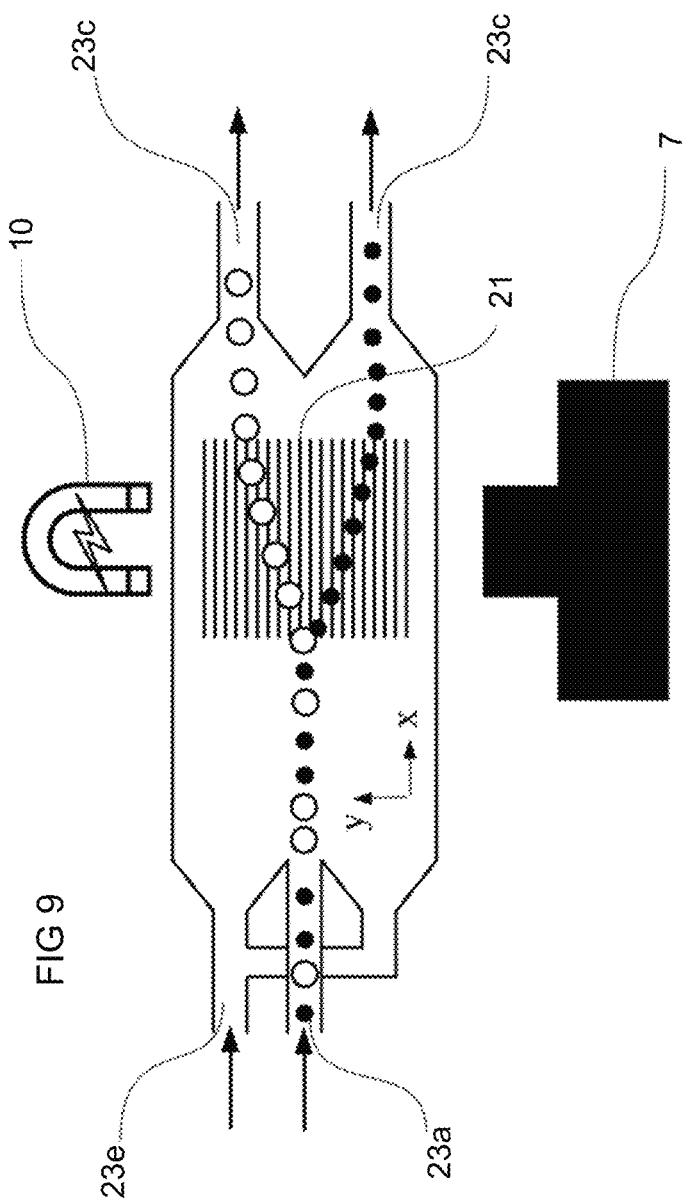
FIG. 9 is a schematic representation of a dielectrophoresis cartridge according to a variant.

In another embodiment, as illustrated schematically in FIG. 9, it is possible to have two outlet channels, a first one corresponding to the return channel 23c and another one corresponding to a waste channel 23d in which non-viable cells are removed from the fluid stream, the viable cells returning to the cell culture medium.

The dielectrophoresis cartridge 5 allowing continuous or semi continuous analysis of cell viability, in combination with the closed circuit connections from the cell culture tank to back to the cell culture tank, using a peristaltic pump or shuttle pump (or other pump type that does not have actuators that contact the liquid medium), ensures on the one hand a sterile liquid circuit while at the same time allowing economical automated analysis of the state of cells in the culture medium. The dielectrophoresis cartridge and cell culture tank are moreover sterilely separated from the monitoring apparatus 3 and they can be economically and easily disposed of while reusing the monitoring apparatus without requirement for special treatment.

The dielectrophoresis cartridge 5 may be coupled to supple tubes forming the supply and return conduits 40a, 40b and removably inserted into a slot of a cartridge holder portion 28 of the monitoring apparatus 3. While in position within the cartridge holder portion 28, the dielectrophoresis cartridge 5 is positioned such that the image capture system 7 and spectrometer 8 are positioned over the measuring chamber 23b, able to capture the movement of cells flowing in the measuring chamber and detect properties of the fluid. The cartridge is provided with a transparent window formed at least over the measuring chamber in the measuring chamber. The transparent window may be formed by the electrode support 19, for instance in a form of a layer of glass, but may also be viewable through a transparent polymer window of the base 20.

In certain variants, light sources 13 may be positioned on an opposite side of the cartridge holder portion with respect to the image capture system 7.

The spectrometer 8 may be used to capture properties of the fluid whereas the image capture system may be used to detect the cells within the liquid to capture the movement of the cells through the measuring chamber.

The computing unit 9 connected to the spectrometer 8 and image capture system 7 is configured with algorithms to count cells and to analyze the trajectory of the cells and determine therefrom the viability of the cells. The computing unit comprises a signal generator 12 connected to the electrodes 21 for generating the traveling wave dielectrophoresis signal. An impedance meter 11 may further be connected to the computing unit 9, the impedance meter measuring the electrical impedance of liquid flowing through the measuring chamber. The impedance meter may comprise two spaced apart electrodes immersed in the culture medium flowing through the cartridge 5.

As best seen in FIG. 7, according to an advantageous embodiment, the multiple electrodes may form a pair of mirror image spirals. In the illustrated embodiment, there are eight electrodes, four on each spiral. The spirals in the illustrated embodiment have a substantially rectangular form, but could have oval or rounded forms. In advantageous embodiments, there may be less electrodes, for instance six or four electrodes.

In an embodiment (not shown), there may however be only a single spiral of the plurality of electrodes.

This spiral shaped measurement portion of the electrodes advantageously allows to reduce the number of electrodes while providing a sufficiently large width application of the traveling wave dielectrophoresis signal, causing easily measurable translation of viable cells.

Reducing the number of electrodes advantageously allows a reduction number of electrodes to be contacted, the contact portions 21b extending and spreading outwardly and increasing in width to provide sufficient contact surface areas for complementary terminals 31a of an electrical connector 31 in the cartridge holder portion 28 of the monitoring apparatus. As best seen in FIGS. 5d and 5c, the connector 31 comprises spring mounted contacts that elastically press against the metallized pads of the electrode contact portions 21b when the dielectrophoresis cartridge 5 is fully plugged into the cartridge holder portion 28.

The cartridge holder portion 28 comprises a cartridge holder slot 29 within which the dielectrophoresis cartridge may be inserted fully into the measurement position, whereby locating elements 30, for instance in a form of protuberances 30a received in corresponding recesses 30b in the base 20 of the dielectrophoresis cartridge, to hold and locate the dielectrophoresis cartridge within the cartridge holder slot 29. The locating elements 30b may be spring mounted in the cartridge holder portion 28, or may be rigid whereby the elastic compliance is provided by the material of the dielectrophoresis cartridge 5, and optionally by providing the dielectrophoresis cartridge with elastic guides and recesses that engage the protuberances on the cartridge holder portion 28.

The monitoring apparatus may be provided with a manually or electrically actuated ejector 33 comprising a pusher mechanism (only schematically represented) to eject or assist ejection of the cartridge out of the cartridge holder slot 29.

The image capture system 7 may comprise an optical microscope 12 coupled to a digital image capture system that allows digital processing of the optical images. In variants it is however possible to employ other image capture systems such as:

phase contrast imaging using a phase contrast microscope as imaging system to increase the contrast of the image and improve the quality of cell recognition.

a confocal microscope as imaging system to increase the resolution of the image, whereby confocal imaging allows to reconstruct a 3D model of cells that improve the quality of cell characterization.

Light sheet microscopy could be used for creating 3D images of the channel inside. It would provide more information about the cell morphology.

In the measuring chamber 23b, lateral guides 27 may be provided either lateral side of the measurement chamber portion in order to determine the precise height of the measuring chamber, i.e. the gap between the electrode support 19 and the floor of the measuring chamber.

The electrode support 19 may be mounted within a recess 25 of the base 20, providing protection for the electrode support 19.

The dielectrophoresis cartridge 5 can thus be easily plugged into the cartridge holder slot 29 and firmly and accurately located within the cartridge holder slot while at the same time establishing contact by the spring contacts 31a of the connector 31 that press against the electrode contact portion 21b through the electrode connection window 22 of the base 20.

The dielectrophoresis cartridge may thus be connected to the supply and return conduits to the culture tank which can be separately prepared and then easily coupled to the monitoring apparatus for a semi-continuous or continuous analysis of cells during a culture period for instance during a two week period during growth of the cells in the culture medium.

The closed circuit configuration and sterile separation of the fluid circulation system from the the monitoring apparatus, allowing automated analysis of the cells by the image capture system connected to the computing unit, without requiring manual intervention, allows for a particularly safe, sterile and economical growth of cells in a culture medium.

One of the main applications of the present invention is to monitor a cell culture in an aseptic way during an expansion phase (e.g. ~2 weeks). The invention provides a sterile single use disposable kit which may be connected to a monitoring device, the disposable kit thrown away after first use. Using a disposable kit that is connected to the monitoring apparatus in a closed loop, allows the system to perform continuous or semi-continuous analyses of the cell culture during the full time of culture. The measured data may be made available through a communications network to follow remotely the state of the cell culture in real time.

Other phases than the expansion phase may also be interesting to monitor, for instance for bioproduction, these phases for example including a Log Phase, a Stationary Phase, and a Death Phase. Dielectrophoresis can detect cells in early apoptotic state. Therefore the transition to death phase can be anticipated.

Operation of the system may comprise the following aspects. A sample is extracted from the cell culture tank and flows through the dielectrophoresis cartridge. The image capture system with a magnification records the cells passing through the measuring (observation) zone observed through a transparent window of the cartridge. In the observation zone, traveling-wave dielectrophoresis is used to manipulate the cells. Different cell populations can be discriminated and also sorted.

Optical and impedance spectroscopy of the medium will allow monitoring of further parameters such as metabolites content. The data generated by these measurements may be analyzed to provide information about the cell culture status.

Cell density may be measured with the image capture system and subsequent image analysis in the computing unit. The volume which corresponds to the observed zone is known. Two dimensions (x and y) can be calculated with the projection model of the optical microscope. The measurement chamber height is known from the mechanical design and counting may thus be done automatically with image recognition algorithms.

Cell viability may be measured with traveling wave dielectrophoresis, by analyzing the trajectories of the cells with the image capture system. Depending on its trajectory, the viability of each cell can be assessed. By correlating this with image analysis, a precise viability percentage of each cell type can be determined.

Cells phenotypes can be discriminated based on their trajectories generated by dielectrophoretic forces. The size, membrane and dielectric properties of the cells play a role in the dielectrophoretic force. The optical properties (shape, absorption) may also be extracted from image processing algorithms executed in the signal processing unit and increase the confidence for cell discrimination. Different cell types can be clustered along the electrodes by applying different signal patterns. Different signal configurations (phase, amplitude, time) may be run and with the feedback of the image capture system and/or with a method of reinforcement learning, the same cells types may be regrouped together. A similar methodology can also be used for sorting.

The ability of discriminating the cells allows to observe if certain populations of cells grow faster than others or grow to the detriment of the needed cells. The culture condition (nutriments, temperature, diluted gazes, pH, metabolite content . . . ) for the needed cells can be improved with the data collected and their analysis. Unwanted cells and other particles (bacteria, viruses . . . ) can also be sorted during the monitoring.

The data provided by the spectrometer and impedance meter coupled with other data provided by the system (viability, cell populations . . . ) and data from other devices stored in a communications network may be used in addition to provide information on the state of the culture. Patterns can be found with algorithms (e.g. machine learning) and prediction can be done on current cultures. The data of a plurality of monitoring recordings can be collected and analyzed in the cloud or in the distributed devices.

LIST OF REFERENCES USED cell culture monitoring system 1
monitoring apparatus 3 image capture system 7
  microscope 12
  light 13
spectrometer 8
Computing unit 9
  signal generator 10
  impedance meter 11
cartridge holder portion 28
  cartridge holder slot 29
  locating elements 30
    spring protuberances 30a
  connector 31
    electrical terminals 31a
  ejector 33
fluid circulation system 4
  dielectrophoresis cartridge 5
    base 20
      electrode connection window 22
      microfluidic circuit 23
        inlet channel 23a
        measuring chamber 23b
        raised floor 26
        lateral guides 27
        return channel 23c
        waste channel 23d
        supplementary inlet channel 23e
        outlet (return) 24b
        inlet (supply) 24a
      locating recess 30b
      support mounting recess 25
    electrode support 19
      electrodes 21
        measurement zone 21a
        contacts 21b
  supply conduit 14a
  exit/return conduit 14b
  tank supply/return fluidic connections 16
    perforated tube 17
    fluidic connector 18
      supply connection 18a
      return connection 18b
  pump 6
cell culture tank 2
  cell culture medium 15

The invention claimed is:

1. A cell culture monitoring system comprising:
a monitoring apparatus configured for coupling to a cell culture tank containing a cell culture medium comprising cells therein; and
a fluid circulation system configured for fluidic coupling to the cell culture tank, the fluid circulation system comprising:
supply and return conduits, and
a dielectrophoresis cartridge configured for connection to the cell culture tank via said supply and return conduits, the dielectrophoresis cartridge comprising:
a base and
an electrode support having electrodes in or on the electrode support, the electrodes configured for travelling wave dielectrophoresis and comprising a measurement zone arranged above a measuring chamber formed between the electrode support and a floor of the base forming a measuring chamber therebetween, whereby cells in a liquid medium flowing through the measuring chamber are subject to a travelling wave dielectrophoresis force orthogonal to a direction of flow of said liquid through said measuring chamber,
wherein the monitoring apparatus comprises:
a computing unit,
an image capture system connected to the computing unit, and
a cartridge holder portion for receiving said dielectrophoresis cartridge such that the image capture system may detect cells flowing through said measuring chamber.

2. The system according to claim 1, wherein at least the base of the dielectrophoresis cartridge is made of a transparent polymer.

3. The system according to claim 1, wherein the electrode support is made of a transparent polymer or glass.

4. The system according to claim 1, wherein the dielectrophoresis cartridge comprises an outlet and an inlet configured for coupling to tubes of a polymer forming said supply and return conduits.

5. The system according to claim 1, wherein the monitoring apparatus comprises complementary spring contacts and wherein the electrodes are formed on an inner surface of the electrode support bounding the measuring chamber and having contact portions extending to an electrode connection window formed in the base for plugging contact to the complementary spring contacts of the monitoring apparatus, the electrode connection window being sealingly separated from the measuring chamber.

6. The system according to claim 1, wherein the measuring chamber comprises a raised floor and lateral guides defining a gap between the floor and electrode support.

7. The system according to claim 1, wherein said electrodes comprise a measurement zone formed by one or more spiraling conductive tracks.

8. The system according to claim 1, wherein said electrodes consist of four to ten electrodes.

9. The system according to claim 1, wherein the electrodes are arranged in the measurement zone in two sets in mirror image symmetry.

10. The system according to claim 1, wherein the cartridge holder portion of the monitoring apparatus comprises a cartridge holder slot configured for slidable insertion of the dielectrophoresis cartridge therein.

11. The system according to claim 1, wherein the cartridge holder portion comprises locating elements engaging in complementary locating elements in the dielectrophoresis cartridge for positioning and securing the dielectrophoresis cartridge in a measurement position.

12. The system according to claim 11, wherein the locating elements comprises spring protuberances or spring resist portions on either the cartridge holder portion or the di electrophoresis cartridge.

13. The system according to claim 1, wherein the image capture system comprises a microscope connected to an image processing circuit of the computing unit configured for digital analysis of the trajectory of the cells captured by the image capture system.

14. The system according to claim 1, wherein the computing unit comprises a signal generator connected via a connector to the electrodes of the dielectrophoresis cartridge configured to generate a travelling wave dielectrophoresis signal in the measurement zone of the electrodes.

15. The system according to claim 1, wherein a gap in the measuring chamber between electrode and floor is in the range of 10 to 200 µm.

* * * * *